United States Patent [19]

Heimann

[11] Patent Number: 5,035,247
[45] Date of Patent: Jul. 30, 1991

[54] SENSOR FOR NON-INVASIVE MEASUREMENT OF SOUND, PRESSURE AND VIBRATION ON THE HUMAN BODY

[76] Inventor: Jochen Heimann, Leonhardistr. 10a, D-8011 Siegertsbrunn, Fed. Rep. of Germany

[21] Appl. No.: 291,513

[22] Filed: Dec. 29, 1988

[30] Foreign Application Priority Data

Dec. 31, 1987 [DE] Fed. Rep. of Germany ....... 3744605

[51] Int. Cl.$^5$ ............................................... A61B 5/02
[52] U.S. Cl. .................................... 128/715; 128/701; 128/773
[58] Field of Search .................... 128/715, 773, 701

[56] References Cited

U.S. PATENT DOCUMENTS

| | | | |
|---|---|---|---|
| 3,233,041 | 2/1966 | Croslin | 128/715 |
| 3,387,149 | 6/1968 | Young | 128/715 |
| 3,921,623 | 11/1975 | Okada et al. | 128/715 |
| 4,220,160 | 9/1980 | Kimball et al. | 128/715 |
| 4,947,859 | 8/1990 | Brewer et al. | 128/715 |

Primary Examiner—Francis Jaworski
Assistant Examiner—George Manuel
Attorney, Agent, or Firm—W. Norman Roth

[57] ABSTRACT

The invention relates to a sensor (1) for non-invasive measurement of sound, pressure and vibration on the human body which features a transducer in the form of a transducer membrane (23) to achieve a very good response characteristic coupled with low weight and small size. The transducer diaphragm (23) is preferably configured as a piezoelectric foil which converts the mechanical input variables into electrical signals which can be processed by means of processor units.

19 Claims, 1 Drawing Sheet

SENSOR FOR NON-INVASIVE MEASUREMENT OF SOUND, PRESSURE AND VIBRATION ON THE HUMAN BODY

BACKGROUND OF THE INVENTION AND PRIOR ART

1. Field of the Invention

This invention relates to a sensor for non-invasive measurement of sound pressure and vibration on the human body.

2. Description of Prior Art

Such a sensor is known from the brochure "Kreislaufkontrollem mit den Infraton-Pulsabnehmer" (System: Boucke-Brecht) describing a pulse pickup. This pickup (sensor) features a probe which is effective with respect to a special-type capacitive winding and winding core arranged in an enclosure. The core of the capacitor is surrounded by an internal rubber jacket incorporating an air cushion. The rubber jacket is enveloped by silver wire meshing which is, in turn, surrounded by an outer rubber jacket around its outer surface.

This sensor is an electrostatic transducer of high capacitance which can be attached by bindings or bandages to suitable parts of the human body as a pulse pickup.

Other known sensors, particularly those used in cardiac sound measurements, feature a probe in conjunction with a lever mechanism for transmitting the deflection of the probe to an mechanoelectrical transducer. Sensors of this kind are a disadvantage particularly because they are large and relatively heavy and thus incondusive to the condition of the patient where applied to the surface of the body,, therefore, making measurements possible practically only when the patient is resting This, in turn restricts the scope of application of said known sensors since dynamic measurements, for instance when the patient is moving, are almost impossible or only with considerable impedance to the person concerned.

SUMMARY OF THE INVENTION

It is, therefore, the object of the present invention to create a sensor of light weight and whose dimensions are small to avoid it obstructing the measurement.

This object is achieved by a sensor for non-invasive measurement of sound, pressure and vibration on the human body comprising:

a sensor cell featuring a probe which can be placed on the surface of said body to sense mechanical input variables, a transducer which is coupled to said probe and which converts said mechanical input variable into an electrical signal, a transmission device connected to said transducer and a signal preamplifier connected via said transmission device to said transducer and which can be connected to a processing unit, whereby said transducer is a transducer diaphragm.

Configuring the transducer as a transducer diaphragm enables the sensor as the object of the invention to be extremely compact and light in weight resulting in said sensor being in no way an obstruction when applied to the human body, i.e. to the wearer. It is, therefore, possible with no problem whatsoever to also carry out measurements on the wearer under dynamic loading conditions, for instance, when the wearer is required to execute movements of various kinds.

Due to the right weight of the sensor very good measurement characteristics are obtained which produce very accurate results when using the sensor as the object of the present invention.

Experimental testing has been carried out to achieve the design criteria. Proximity measurements using a laser doppler arrangement have indicated that the mass of the sensor in sound and vibration measurements distorts the deflection variable to be measured on the surface of the body. Optimized measurement signals can be obtained as regards the frequency-dependent swing of the signal and as regards the band width of the signal by not only reducing the mass of the sensor but also the amount of contact pressure of the sensor at the point of measurement. Further tests carried out within the framework of the invention have indicated that the information contained in the standard reference literature regarding the amount of contact pressure to the sensor produces mechanical loading of the point of measurement which causes nonlinear attenuation at the point of measurement. Sensors of high inherent mass and configuration causing a high contact pressure partly resulting from the high inherent weight of the sensors or from the tensioning straps of belts, serving to secure the sensors, do not permit a reliable diagnostic interpretation of cardiac murmur contained in the higher frequencies of the heart sound signal.

BRIEF DESCRIPTION OF THE DRAWING

Some embodiments of the invention will now be described by way of example and with reference to the accompanying drawings in which.

DESCRIPTION OF THE PREFERRED EMBODIMENT

Figure 1:
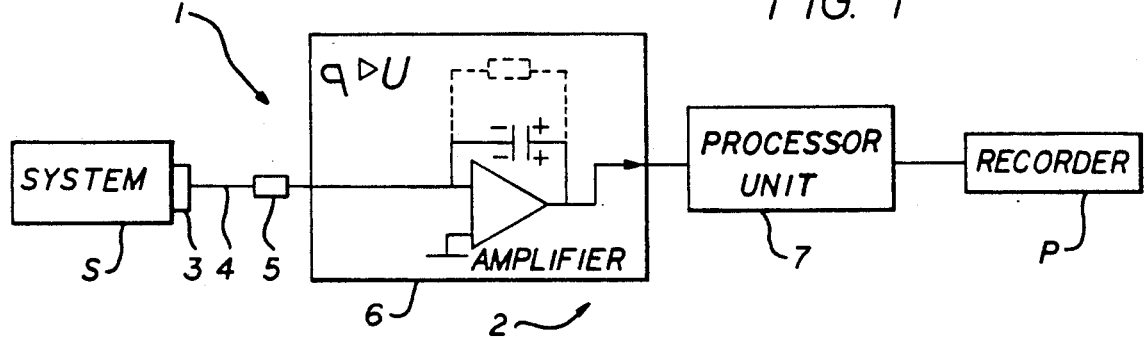
FIG. 1 is a block diagram involving the sensor as the object of the invention.

FIG. 1 is a schematic simplified illustration of a sensor 1 in accordance with the present invention forming part of a measuring circuit 2. Sensor 1 features, as shown in FIG. 1, a sensor cell 3 applied to a system S to be measured which can be, for example, the human body for the purpose of detecting sound, such as for instance heart sound, pressure and vibration. The sensor 1 can be allied to the human body S for example by means of a body-compatible slightly tacky substance since it is extremely light and small. The sensor cell 3 is connected via a very short cable 4 and a connector 5 to an active charge amplifier 6. The active charge amplifier which functions as a signal preamplifier is connected by its output via a lengthy cable to a processor unit 7 which, in turn, may be connected to a recording and output unit such as, for instance, a recorder P.

In the aforementioned circuit 2 the sensor 1 is formed by the following detailed sensor cell 3, the cable 4 constituting a transmission device, and the signal preamplifier 6.

In the aforementioned arrangement the cable 4 should be maintained as short as possible, its length in the extreme case being shortened to zero, meaning that the preamplifier 6 is arranged in or on the sensor cell 3.

In addition, the cable 4 should have a high insulation resistance and a low capacitance to minimize the dielectric losses. Cable 4 is preferably provided as a coaxial cable for advantages as regards screening from noise.

The transmission device 4 and the preamplifier 6 can be further combined into a wireless transmission device. This has the advantage that there if no need to carry the connecting cables in some application as in long-term and/or intensive monitoring of patients in mobile as well as in stationary operation.

The wireless transmission device can take the form of a high-frequency transmitter, the carrier signal of which is modulated by the measurement signal (input). This arrangement should, however, contain measures for selectivity to permit, e.g. reception of the signals obtained from individual patients via a central receiver and separation according to channel, i.e. an additional high-frequency intermediate carrier or channel-selective signal coding in making use of the advantages of digital signal transmission. Devices of this kind for signal coding are adequately described in communications system engineering.

In a further embodiment the wireless transmission device can take the form of an infrared or laser transmitter device; too the measures for channel-specific selection of the individual patient signal values as explained in the previous paragraph apply. A digital signal transmission device is particularly advantageous in this case, since considerable energy savings are to be had by suitably selecting the mark/space ration of the digital pulse signals. Mark-to-space ratios of 1:10 through 1:100, depending on the technical design of the infrared or laser transmission device and how far the transmitter can reach, are technically feasible.

In low power supply situations, the digital sensor date can also be transmitted via optical waveguide cables. Taking into account the measures of multiple utilization of a transmission device as described above the sensors applied to the patient can be hooked up via a transmission device either by a high-frequency transmitter and/or in wireless transmission by an optical transmission device or via a cable or an optical waveguide cable; the modulation device then handling selection of the individual sensor signals upstream of the transmission device.

For digital transmission of the sensor signals the analog measurements signals of the transducer must be converted into digital signals of the transducer. Methods of doing this are sufficiently known from pertinent technical literature. for this purpose it is of advantage to provide for serial output of the digital values of the converter, since a parallel output necessitates additional expense as regard transmission devices.

Preferably the signal preamplifier 6 and the analog/-digital converter are combined into a single functional unit; e.g. by using a charge/frequency converter in which the charge amount of the mechanoelectrical converter is directly converted into a frequency-proportional signal.

Figure 2:
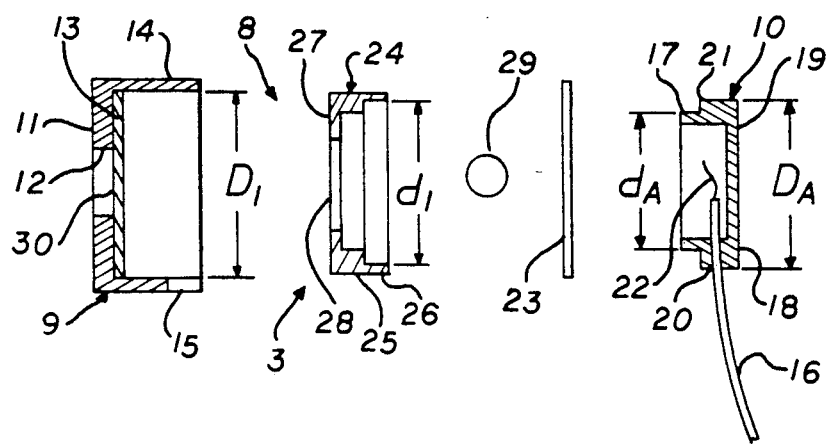
FIG. 2 is a schematic illustration of a simplified exploded cross-section through a first embodiment or the sensor suitable for use in the circuit as shown in FIG. 1.

The following describes a first embodiment of the sensor cell shown in FIG. 1 on the basis of FIG. 2.

Sensor cell 3 illustrated in FIG. 2 exploded features an enclosure 8 comprising an electrically conducting first part 9 and an electrically non-conducting second part 10.

As can be seen from FIG. 2 the electrically conducting first part of the enclosure 9 has a dynamically balanced pot-shaped configuration, it featuring a central opening 12 in its front plate 11. As used herein, the term "dynamically balanced" refers to a geometric shape generated by the rotation of a line about an axis of rotation, e.g., to generate a shape such as a cylinder or cone. On the inside of the front plate 11 a spring element 13 in the form of a flexible diaphragm is secured which fully seals off the opening 12. The first enclosure part 9 also features in its peripheral annular wall 14 a further opening 15 through which a connecting lead 16 can be introduced in the fitted condition of the sensor cell 3. Since the first enclosure at 9 is formed electrically conducting, it is preferably made of brass. The surface of the first enclosure part p must be additionally coated to be resistant to disinfectants and cleansants. Finish-coating the surface in this way can be achieved by nickel or chrome plating.

The cover-type second part of the enclosure 10 of electrically non-conducting material can be made of PVO for instance. However, the plastic used must have mechanical and chemical properties which remain unchanged due to contact with disinfectants and cleansants. In addition, this plastic should be impervious to changes in temperature to a certain degree so that the patient is not exposed to any gas release from the plastic. In detail the second enclosure part 10 also features a dynamically balanced shape with an outer diameter $D_A$ which, depending the tolerance requirement, is either in accordance with the internal diameter $D_x$ of the first enclosure part 9 or is somewhat larger. In addition, the second enclosure part 10 features an annular-shaped collar 17, the outer diameter of which $d_A$ is smaller than the outer diameter $D_A$ whereas the internal diameter of the two parts is the same. In a front outer wall 18 of the second enclosure part 10 an opening 19 is provided which serves as a pressure offset port. The cable 16 is inserted through opening 20 in an annular wall area 21 of the second enclosure part 10 into its interior where it is secured. For this purpose a bright end 22 is arranged in such a way that it can be connected, e.g. by bonding to a transducer in the form of a transducer diaphragm 23.

The transducer diaphragm 28 is preferably provided as a piezoelectric foil which can consist, e.g. of a plastic carrier vacuum coated on both sides with an electrically conducting film. As detailed by FIG. 2 the foil is essentially flat before it is fitted and is also dynamically balanced, preferably circular in shape. Fitting the foil 23 is described in more detail in the following:

The sensor cell 3 also features a clamping ring 24 which is also dynamically balanced and which acts in conjunction with the second enclosure part 10 when assembled in place. The clamping ring 24 has a base area 25 of larger wall thickness opposite an annular area 26. The annular area 26 has an internal diameter $d_1$ which can essentially correspond to the outer diameter $d_A$ or the ring area 17 of enclosure part 10. Since the diaphragm 23 is tensioned between the clamping ring 24 and the second enclosure part 10 it is possible to achieve differing pretensions of the diaphragm 28 in the coarse of installation or tensioning it by forming the flanks of the annular area 26 and the annular area 17. This means in other words that a high pretension can be achieved when the tolerances are tight, which means that the internal diameter of the clamping ring 24 is essentially the same as the outer diameter of the annular area 17 of the second enclosure part 10 whereas the pretension is reduced as the internal diameter of the clamping ring 24 increases. These fitting parameters can be selected in this way because the transducer diaphragm 23 is only a few micrometers thick. In addition, for vernier adjustment it is possible to bevel the areas of the clamping ring 24 or of the second enclosure part 10 in sliding contact with each other, i.e. to configure their slope differently.

The clamping ring 24 also features circular opening 28 in its area 27 which is in contact with the diaphragm 13 when fitted.

In conclusion, the sensor cell 8 features a spherical or ellipsoidal probe 29 in the embodiment example. This probe 29 serves to sense the mechanical input variable and is thus applied to the surface of the body when in use.

When the sensor cell 3 shown in an exploded view in FIG. 2 is assembled the probe 29 — after fitting the spring element 13 in the first enclosure part 9 — is center-mounted on the spring element 13, i.e. with respect to the opening 12. The diaphragm 23 is then clamped to the second enclosure part 10 by using the clamping ring 24 and applying pressure. This unit is then inserted in the first enclosure part 9. Since the spring element 13 projects radially to a slight degree over the second enclosure part 10 and the clamping ring 24, an electrical contact is produced with the first enclosure part 9 when the unit (24, 10, 23) is inserted. This is why it is merely necessary, to close the electrical circuit, to connect the shielding GND of e.g. a coaxial cable used as the transmission device 4 to the first enclosure part 9 electrically. For this purpose, the diaphragm 23 — in the aforementioned ways and means is pretensioned both by the interaction of the clamping 24 and the second enclosure part 10 and by the effect of the probe 29 due to it being in contact with the flexible spring element 13. In this arrangement the probe 29 and the corresponding part of the spring element 13 protrudes through the exit opening 12 so that it protrudes past the outer surface of the front plate 11 when the sensor cell 3 is assembled and thus the probe 29 is coupled to the pretensioned diaphragm 23.

In this arrangement the rigidity of the diaphragm 13 forming the spring element is less than the rigidity of the transducer diaphragm 23. Preferably the rigidity of the spring element 13 amounts to 10 through 30% of the rigidity of the transducer diaphragm 23. In addition, the mass of the probe 29 is much less than that of the enclosure. In a particularly preferred embodiment the mass of the probe amounts to 0.02 g whereas that of the enclosure is approximately 1.68 g. the ratio of probe mass to enclosure mass for the various embodiments ranges from 1:10 to 1:30.

The total mass of the sensor cell is all in all very low and generally amounts to less than 2 g.

In addition, it should be noted that the pressure offset port is much smaller (e.g. 0.5-0.8 mm) than that the wavelength received of the physical variable (sound, pressure vibration) to be sensed.

As described, the probe 29 protrudes past the outer surface of the enclosure 8 when sealed in the fitted condition by the spring element 13, so that it is capable of sensing mechanical movements of, for example, the body surface produced by sound, pressure and vibration. These detected mechanical input variables are transmitted from the probe 29 to the piezoelectric diaphragm 23 forming the transducer, the diaphragm in turn converting the mechanical input variable into an electrical signal. The electrical signal is passed via the transmission device e.g. in the form of cable 4 to signal preamplifier 6 which produces amplification of the signal by means of the circuit arrangement shown for example in FIG. 1 to which express reference is made of reasons of disclosure.

In the processor unit 7 and the recorder P the sensed signals can then be evaluated for measurement and output.

Figure 3:
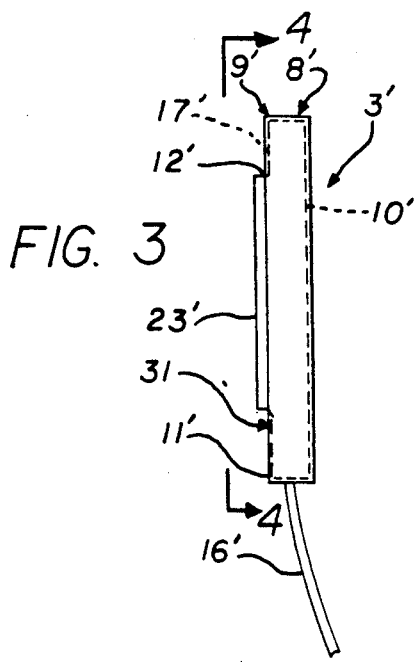
FIG. 3 is a side view of a second embodiment of the sensor suitable for use in the circuit ass shown in FIG. 1.
Figure 4:
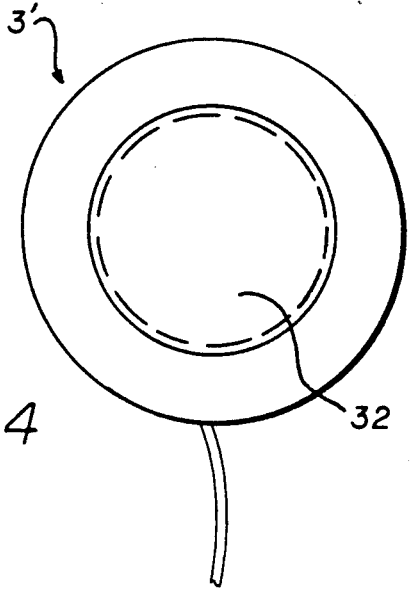
FIG. 4 is a plan view of the sensor as shown in FIG. 3 in the directions of the arrow IV in FIG. 3.

In the following a second embodiment of a sensor cell 3' is described on the basis of FIGS. 3 and 4.

Sensor cell 3' also features an electrically conducting first enclosure part 9' and an electrically non-conducting second enclosure part 10. The first enclosure part 9' is essentially configured just the same as the first enclosure part 9, except that is has a much larger outer diameter and an opening 12' which is also much larger in diameter than the corresponding diameter of the embodiment as shown in FIG. 2. The configuration of the second enclosure part 10' is essentially the same as that of the second enclosure part 10 and thus reference can be made to FIG. 2 for the corresponding configuration of the embodiment.

Sensor cell 3' also features a transducer diaphragm 23' which preferably takes the form of a piezoelectric foil also. The transducer diaphragm foil 23' is contacted by a connecting lead 16' introduced into the enclosure 8'. As can be seen from FIG. 4, sensor cell 3' is also dynamically balanced, whereby when fitted the transducer diaphragm 23' projects past the outer surface 31 of the electrically conducting first enclosure part 9'. In this arrangement the pretension is also produced by the clamping effect between the first and second enclosure parts 9' and 10' whereby the corresponding peripheral collar 17' of the electrically nonconducting second enclosure part 10' when fitted, protrudes through the opening 12' and past the surface 31. The correspondence area 32 of the transducer diaphragm 23' is tensioned when the sensor cell 3' is assembled and arranged paced away from the surface 31 so that it — contrary to the embodiment shown in FIG. 2 — forms both the probe and the transducer. This has the advantage of producing a particularly simple but nevertheless highly sensitive configuration of the sensor cell 3', it being possible to eliminate a separate probe. Accordingly the sensor cell 3' can also be configured even lighter. On the other hand it is also possible to additionally use a clamping ring as shown in FIG. 2, if required.

As regards all identical details and functioning reference can be made to the description of sensor cell 3, shown in FIG. 2.

Persons skilled in the art will readily appreciate that various modifications can be made from the preferred embodiment thus the scope of protection is intended to be defined only by the limitations of the appended claims.

What is claimed is:

1. A sensor for non-invasive measurement of sound, pressure and vibration on the human body comprising:
   a sensor cell featuring a probe which can be placed on the surface of said body to sense mechanical input variables;
   a housing providing an enclosure;
   a transducer comprising a piezoelectric foil diaphragm located in said enclosure with the transducer being coupled to said probe and which converts said mechanical input variables into an electrical signal;

a transmission device connected to said transducer; and a signal preamplifier connected via said transmission device to said transducer and which can be connected to a processing unit, said housing having a pressure offset port which is smaller than the wavelength to be received.

2. A sensor as claimed in claim 1 wherein said enclosure comprises an electrically conducting part and an electrically nonconducting part.

3. A sensor as claimed in claim 4 wherein said enclosure is dynamically balanced.

4. A sensor as claimed in any of claims 1 through 3 wherein said probe penetrates a wall of said enclosure and projects therefrom.

5. A sensor as claimed in any of claims 1 through 4 wherein the mass of said probe is much smaller than the mass of said enclosure.

6. A sensor as claimed in claim 5 wherein the total mass of said sensor is less than 2 g.

7. Sensor as claimed in any of claims 1 through 6 wherein said transmission device is a short cable.

8. Sensor as claimed in claim 7 wherein said cable has a high insulation resistance and a low capacitance.

9. Sensor as claimed in claim 2 wherein said electrically conducting part of said enclosure is of brass.

10. Sensor as claimed in claim 2 wherein said non-electrically conducting part of said enclosure is of PVC.

11. Sensor as claimed in any of claims 1 through 10 wherein said signal preamplifier is an active charge amplifier.

12. Sensor as claimed in any of claims 1 through 11 wherein said signal preamplifier is located on said housing enclosure.

13. Sensor as claimed in any of claims 1 through 12 wherein said probe is coupled to said transducer by a spring element.

14. Sensor as claimed in claim 13 wherein the rigidity of said spring element is less than that of said transducer diaphragm.

15. Sensor as claimed in claim 13 or 14 wherein said spring element is a flex diaphragm.

16. Sensor as claimed in any of claims 1 through 15 wherein said probe is spherical or ellipsoidal.

17. Sensor as claimed in any of claims 1 through 12 wherein said probe and said transducer are a single member.

18. Sensor as claimed in claim 17 wherein said member is a piezoelectric transducer diaphragm.

19. Sensor as claimed in claim 17 or 18 wherein said diaphragm is tensioned between said enclosure parts.

* * * * *